United States Patent [19]
Keller

[11] Patent Number: 5,129,824
[45] Date of Patent: Jul. 14, 1992

[54] METHOD FOR TREATING PERIODONTAL DISEASE

[76] Inventor: Duane C. Keller, 62 Grantwood, St. Louis, Mo. 63123

[21] Appl. No.: 454,430

[22] Filed: Dec. 21, 1989

[51] Int. Cl.$^5$ ............................................. A61C 5/00
[52] U.S. Cl. .................................................. 433/215
[58] Field of Search .................. 132/321, 323; 424/52; 433/80, 215

[56] References Cited

U.S. PATENT DOCUMENTS

| | | | |
|---|---|---|---|
| 3,844,286 | 10/1974 | Cowen | 128/861 |
| 3,879,139 | 4/1975 | Dahl et al. | 15/22 |
| 3,896,824 | 7/1975 | Thornton | 132/321 |
| 3,964,164 | 6/1976 | Hesselgren | 433/217.1 |
| 4,162,688 | 7/1979 | Tarrson et al. | 132/322 |
| 4,175,326 | 11/1979 | Goodson | 433/80 |
| 4,411,889 | 10/1983 | Caslansky et al. | 424/52 |
| 4,499,068 | 2/1985 | Silbering et al. | 424/52 |
| 4,685,883 | 8/1987 | Jernberg | 433/215 |
| 4,691,404 | 9/1987 | Tarrson et al. | 15/167.1 |
| 4,892,736 | 1/1990 | Goodson | 433/80 |
| 4,911,927 | 3/1990 | Hill et al. | 132/323 |

FOREIGN PATENT DOCUMENTS 0114113 7/1984 European Pat. Off.

Primary Examiner—John J. Wilson
Attorney, Agent, or Firm—Polster, Lieder, Woodruff & Lucchesi

[57] ABSTRACT

A method of and system for the treatment of periodontal diseases is disclosed wherein a patient, using a delivery device, applies a medicament directly to the infected site. The delivery device may comprise a piece of tufted dental floss, an interdental brush, a syringe, or a night time application tray for forcibly applying medicament to the infected site. The delivery device carries a supply of an antimicrobial or antibiotic medicament, preferably a tetracycline, dichloride or hydrogen peroxide solution or gel. By flossing, brushing, injecting, or by forcibly disbursing the medicament with the delivery device, the patient can apply the medicament directly on or in close proximity to the infected site (i.e., bony support structure of the teeth). The medicament (tetracycline) bonds with the bony structure to promote bone regeneration, decrease osteoclastic activity and to allow osteoblastic activity to continue with a consequent decrease in bone loss rate while promoting bone growth (regeneration). Through the use of an oxygenation agent (hydrogen peroxide), fluoride, dichloride, or other medicaments, microbial activity, plaque development, and pathologic processes are decreased.

7 Claims, 4 Drawing Sheets

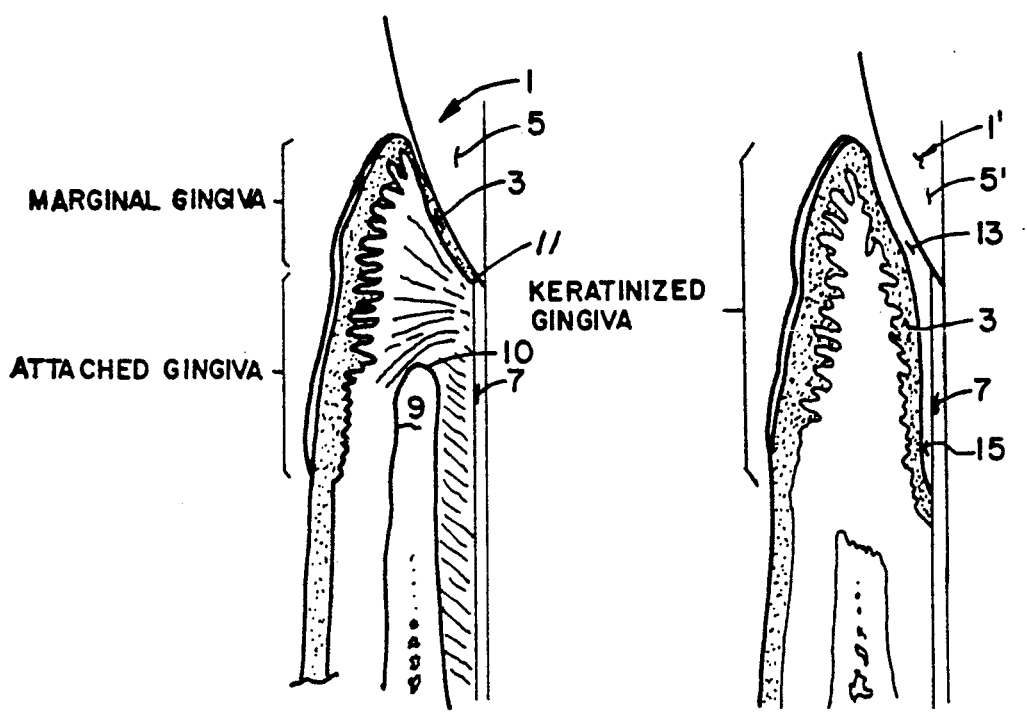
FIG. 1.
HEALTHY
FIG. 2.
DISEASED,
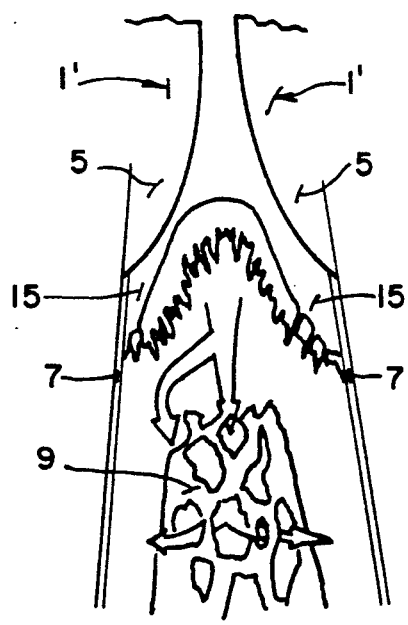
FIG. 3.
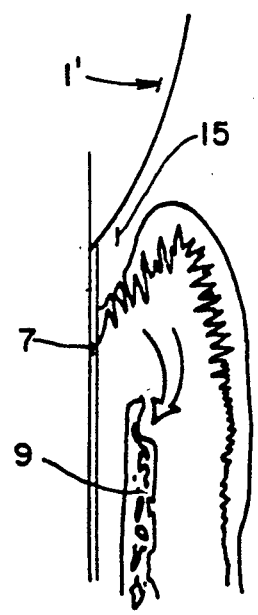
FIG. 4.

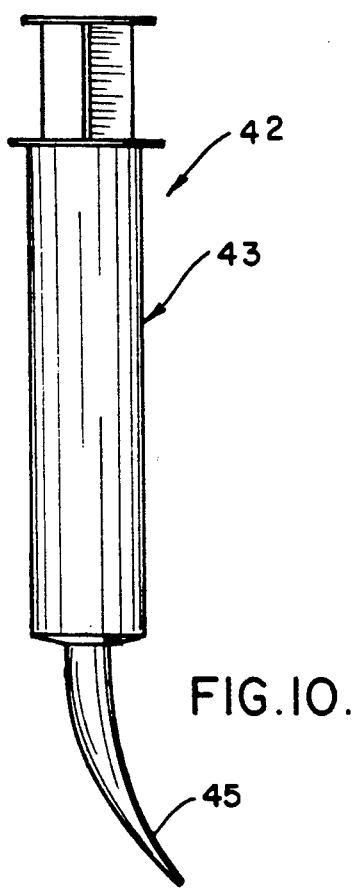
FIG.10.
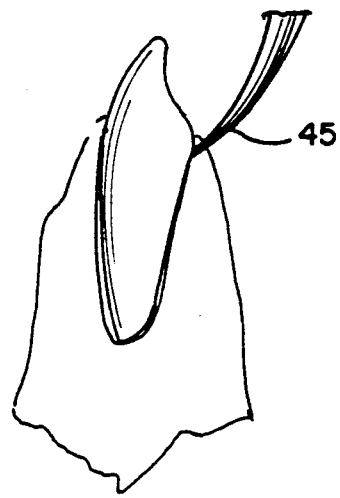
FIG.11.
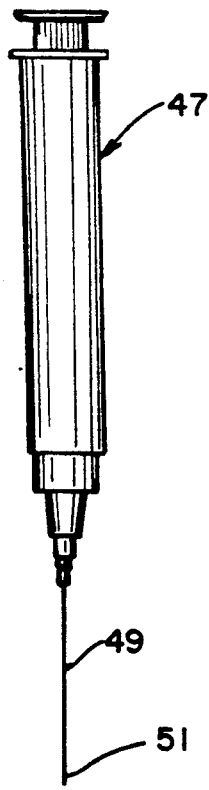
FIG.12.
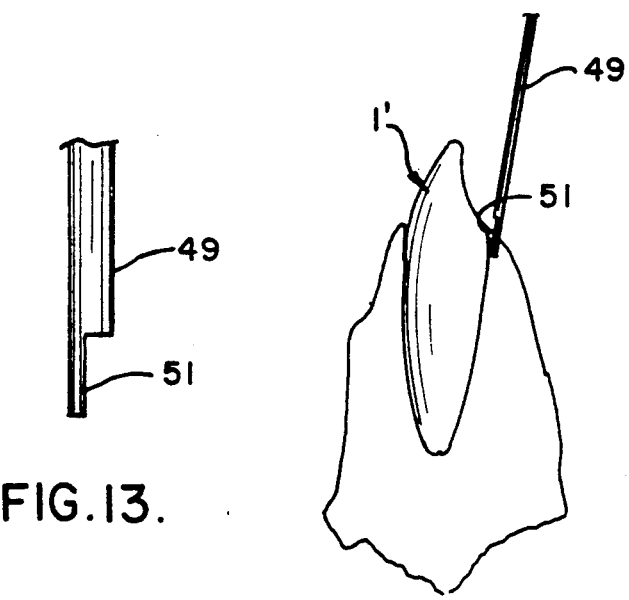
FIG.13.
FIG.14.

METHOD FOR TREATING PERIODONTAL DISEASE

BACKGROUND OF THE INVENTION

This invention relates to a method of and a system for the treatment of periodontal disease, and, in particular, to the delivery of medication directly to the source of the infection.

Periodontal disease may be caused by microbes utilizing food which is impacted into the gingival crevice or by occlusal trauma. Periodontal disease may also be caused by restorations having rough edges or interproximal overhangs which allow for the build up of bacteria on the rough edges or around the margins of the excess material of the overhang or other causes. Periodontal disease may result in inflammation of the gingival unit and may extend to the periodontal ligament, the aveolar bone and the cementum. It may lead to loss of clinical attachment and aveolar bone, ultimately resulting in the loss of teeth and the need for dental prosthesis.

Several methods have been used to treat periodontal disease. These include root planing, gingivectomy, chemical wettage, and osseous resective surgery. Root planing, gingivectomy and osseous resective surgery all involve surgical removal of infected bone or tissue. Chemical wettage involves the delivery of a solution of various agents, e.g., Vitamin C and hydrogen peroxide, to the infected area by irrigation, syringe or rinse. A topical tetracycline rinse has also been used. The chemical wettage solution and tetracycline topical rinse have been used in combination with other medications to impede bacterial and microbal growth and to allow healing. However, because of the delivery methods used with these prior chemical wettage and topical rinse treatments, these treatments generally have not been effective in the treatment of periodontal disease.

Heretofore, cords chemically treated or impregnated with medicaments (e.g., tetracycline or other agents) have been applied under the gingiva by a dentist. Typically, a small length of such chemically treated cord is forced under the gingiva and allowed to remain in place for an extended period of time (up to ten days or so). It is necessary for the dentist to remove these cords.

The prior art discloses many methods of delivering a medicament for the treatment of periodontal disease. U.S. Pat. Nos. 3,844,286 to Cowen, 3,964,164 to Hesselgren, and 4,411,889 to Caslavsky et al. disclose methods and devices for the topical delivery of medication to the teeth, gums, and pockets. Cowen uses a flexible I-beam shaped foam bar which may carry a fluoride, a phosphate, or an antibiotic. The medication which is carried by the bar is released by mastication (biting) pressure. Hesselgren uses a moldable carrier, such as wax or rubber, which includes an activator. Medications, such as fluoride, are mixed in with the carrier which is then applied to the outside of the teeth and gums using a mold to form a molded mass around the teeth. Caslavsky et al. discloses a self-gelling aqueous solution which topically delivers fluoride, antibiotic, or antibacterial agents. These above-mentioned prior art patents concern the delivery of a medication to the tooth, gums, or periodontal pockets. However, none of the prior delivery methods delivered the medication directly to the source of the infection near or at the bony structure supporting the teeth.

EP Pat. Appln. No. 0,114,113 to Wiley discloses a wooden cleaner for removing material from periodontal pockets, sulci, and tooth surfaces. The cleaner may carry antibiotic medicaments for delivery to the pockets. However, because of the the relative non-absorbent characteristics of the wooden cleaner and the slow rate at which a wooden carrier would release the medication, this delivery device is not believed to be capable of delivering sufficient quantities of the medication. This delivery device is further believed to be unsuitable because it would be difficult to make it flexible enough to deliver medication to the bony structure.

U.S. Pat. No. 4,162,688 to Tarson et al discloses a device for applying medication, generally, fluoride, to dental floss. Although the dental floss is flexible, Tarson et al do not disclose direct delivery of medication to the bony structure, and the floss disclosed is not sufficiently absorbent to hold an adequate amount of medicament to be effective.

The dental community has recognized the need to regenerate the support structures of the teeth in the treatment of periodontal disease. In the October, 1989 issue of the *Journal of the American Dental Association*, at page 484, it is reported that researchers have been using highly osteogenic materials to promote bone regeneration. Such materials include demineralized freeze-dried bone, allograft or cancellous bone and marrow, which, when placed in subcutaneous tissue, promotes bone formation. Other research involves the use of human bone proteins to initiate or enhance bone regeneration.

None of the above references disclose a simple method of treatment, which a patient can self-administer, that will cause the bony structure supporting the teeth to regenerate in order to permit healing of the periodontal disease or to reduce the necessity of or the invasiveness of periodontal or oral surgery.

SUMMARY OF THE INVENTION

Among the several objects and features of the present invention may be noted the provision of a method for the treatment of periodontal disease which effectively impedes deterioration of the bone and gums, eliminates or impedes the growth of microbial pathogens, and promotes regeneration or growth of the supporting structures around the patient's teeth;

The provision of such a method of treatment which will reduce the need for, and the invasiveness of, periodontal and/or oral surgical procedures;

The provision of such a method of treatment wherein a patient can easily, without special training or undue skill, self-administer medication to the infected site so that the patient is not dependent upon a dentist or clinician to administer the medication and continue the treatment over an extended period;

The provision of medicament delivery apparatus which is convenient and easy for the patient to use;

The provision of such delivery apparatus or device which forcefully enables the medicament to be delivered to the infected site below the gingiva; and The provision of such delivery apparatus which is inexpensive and easy to use.

These and other objects will become apparent to those skilled in the art in light of the following description and accompanying drawings.

In accordance with the objectives, generally stated, there is provided a method of treatment of periodontal diseases comprises the delivery of a medicament in close proximity to the bone and supporting structure of the teeth.

The medicament is preferably forcibly delivered directly to the infected site by flossing, brushing, or injection through the use of tufted floss, an interdental brush or syringe, respectively, or by hydrostatic or mastication pressure through the use of a tray appliance or the like. Preferably, the flossing or brushing application is carried out using a piece of floss or an interdental toothbrush which carries a supply of the medicament. The floss preferably has tufted section which enhances the carrying capability of the floss. The application of medicament by floss or interdental toothbrush may be supplemented by application of the medication in a flexible tray appliance molded of a suitable synthetic resin material or elastomeric material to conform to the patient's teeth so as to fit closely on the teeth and supporting structure.

Preferably, the medicament used with the floss or brush delivery device is an antibiotic, such as a tetracycline solution. The medicament used with the tray delivery device is preferably a combination of a tetracycline solution and a hydrogen peroxide (oxygenator) gel such that as the hydrogen peroxide decomposes into oxygen and water within the gap between the patient's teeth and the form fitted tray, the antibiotic is forced by hydrostatic pressure beneath the gingiva directly to the infected site. The oxygen rich environment within the tray appliance resulting from the decomposition of the hydrogen peroxide decreases the activity of anaerobic microorganisms in the gingiva area. Antiplaque medications may also be used to decrease plaque build-up.

BRIEF DESCRIPTION OF THE DRAWINGS

FIG. 1 is a cross-sectional view of a healthy tooth;

FIG. 2 is a cross-sectional view of a periodontal diseased tooth showing keratinized gingiva partially separated from its adjacent tooth;

FIGS. 3 and 4 show the progression of periodontal disease and the deterioration of the aveolar crest;

FIG. 10 is a perspective view of a syringe having a bent application nozzle supplemental delivery of medicament to the bony structure below the gingiva;

FIG. 11 is a perspective view of the nozzle of the syringe shown in FIG. 10 to delivering the medicament directly to the bony structure supporting the teeth;

FIG. 12 illustrates a syringe having a blunt applicator tube for delivery of the medicament below the gingiva;

FIG. 13 is an enlarged view of the applicator tube of the syringe shown in FIG. 12 having a portion of the sidewall removed so as to aid in delivery of the medicament to the infected site;

FIG. 14 is a view of a tooth illustrating the delivery of the medicament to the infected site by the applicator tube shown in FIGS. 12 and 13;

Corresponding reference characters indicate corresponding parts throughout the several views of the drawings.

DESCRIPTION OF PREFERRED EMBODIMENTS

Figure 5:
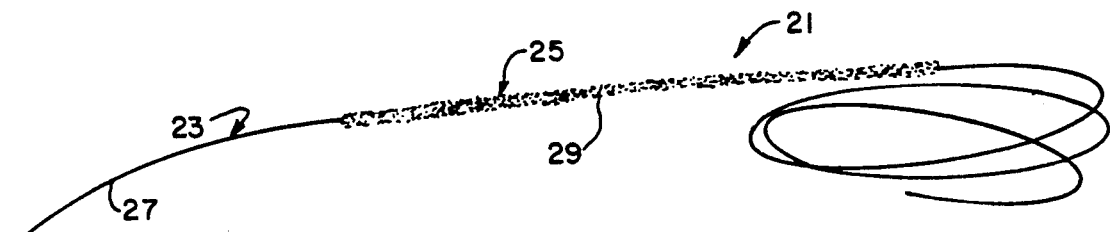
FIG. 5 illustrates a length of tufted floss holding a supply of medicament which may be used in accordance with this invention to deliver the medicament directly to the bony structure supporting the teeth.

Referring now to the drawings, FIG. 1 shows a healthy tooth, as generally indicated at 1. It is seen that a healthy tooth has junctional epithelium 3 covering the enamel 5 of the tooth 1, and that the tooth cementum 7 is not exposed. The aveolar bone 9 with aveolar crest 10 extends nearly to the cementoenamel junction 11 to form a deep socket for the tooth 1. In comparison, a diseased tooth 1', as shown in FIG. 2, has inflammation from periodontis disease which causes the junctional epithelium 3 to move apically (or toward the apex of the root), exposing the cementum 7 and enlarging the sulcus 13 creating a pocket 15. As the inflammation spreads, the aveolar bone 9 is destroyed. This increases tooth mobility and can lead to loss of teeth. The spread of the inflammation through vascular channels of the aveolar bone 9 is shown by the by the arrows in FIGS. 3 and 4.

The destruction of the bony structure is caused by osteoclastic activity acid/base changes and other reasons. Although there is continuous osteoblastic activity, resulting in bone regeneration, but for various reasons the bone regeneration activity cannot keep up with the osteoclastic, bone destroying activity. In accordance with the present invention, when an antimicrobial medicament, such as a solution of tetracycline, is brought into repeated and direct contact with the diseased bone structure, usually below the gum line, it has surprisingly been found that the osteoblastic activity exceeds the osteoclastic activity resulting in net bone regeneration. In accordance with this invention, it has been determined that the tetracycline (or other medicament) solution slows osteoclastic activity but does not adversely affect osteoblastic activity. The bone regeneration decreases infection and body response to an infection and results in a marked decrease in the need for, and the invasiveness of, periodontal surgery.

Referring to FIGS. 5-8, best results are obtained when a the medicament is delivered directly to the bony structure (i.e., the infected site) daily, and preferably every 8-12 hours. The delivery is simplified by the delivery devices of the present invention (as hereinafter disclosed) which allow the patient to self-deliver the medication quickly without the need for special training and/or equipment.

A first embodiment of a delivery device 21 of this invention is shown in FIG. 5 to comprise a piece of dental floss, as generally indicated at 23, having means 25 for holding a supply of a medicament for direct application to the infected site as the teeth are flossed in the usual manner. Specifically, floss 23 comprises a relatively small diameter string carrier 27 which having an enlarged diameter tufted section 29. Such tufted floss is more particularly described in U.S. Pat. No. 3,896,824 to Thornton, which is herein incorporated herein by reference, and is distributed by Oral-B Laboratories, Inc. of Redwood City, Calif. under the trademark Super Floss. It will be understood that the tufted section 29 could extend along the entire length of floss.

Figure 6:
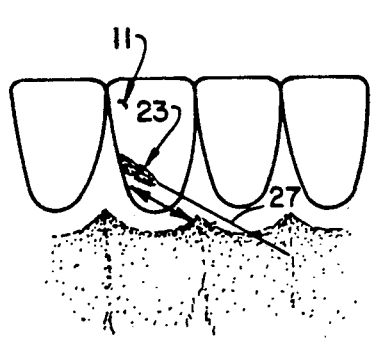
FIG. 6 illustrates the use of the tufted floss of FIG. 5 to deliver the medicament directly to the infected areas.
Figures 7, 8:
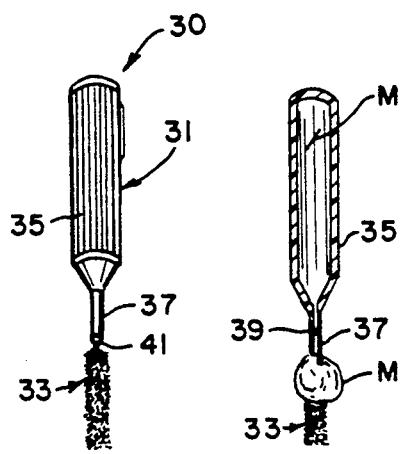
FIG. 7 is a perspective view of an interdental toothbrush housing a supply of medicament which may be used to deliver medicament to the bony structure supporting the teeth.
FIG. 8 is a cross section view of the interdental brush shown in FIG. 7 having a supply of a medicament therein and illustrating a dispensing channel for delivery of the medicament to the brush head.

In FIG. 6, use of the medicated, tufted floss 21 is illustrated. The floss 23 is pretreated so as to hold a supply of a preferred medicament, preferably tetracycline, sufficient to treat all of the patient's teeth. The floss is removed from its packaging (not shown) and is worked by the patient in the usual manner in the interdental spaces such that both the string carrier 27 and the tufted section 29 are forcibly drawn below the gingiva so as to wipe the medicament (tetracycline) carried by the floss directly onto the infected site (e.g., on the aveolar bone 9 and on sulcus 13). The patient should insure that the floss 23 is inserted into the sulcus so the medicament is delivered directly (applied to) to the infected area preferably below the gum line. When delivery device 21 is properly used, the tetracycline solution is deposited directly on, is delivered in close proximity to, or is brought into actual contact with the bony structure of the alveolar bone of the teeth affected by the periodontal disease FIG. 7 shows a second delivery device 30 of the present invention. Delivery device 30 includes an interdental toothbrush 31 having a resilient brush head (i.e., bristle means) 33 mounted on a handle 35. Toothbrush 31 is generally similar to the interdental brush described in U.S. Pat. No. 4,691,404 to Tarson et al, which is also incorporated herein by reference, except for the differences hereinafter pointed out.

In accordance with this invention, interdental toothbrush 31 has a hollow, flexible body 35 holding a supply of medicament M sufficient for at least one treatment of the patient's teeth. Body 35 has a neck 37 carrying brush head 33. As best shown in FIG. 8, a channel 39 extends from the interior of the brush body 35 to brush head (bristle means) 37. A frangible seal 41 closes channel 39 until it is ready for use.

Figure 9:
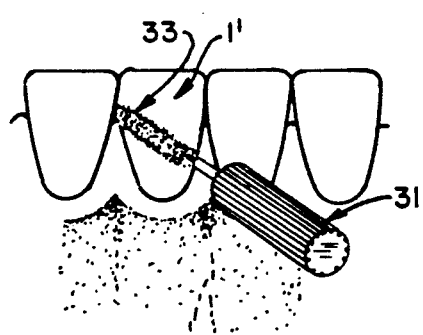
FIG. 9 is a perspective view of the interdental toothbrush of FIG. 7 in use.

In use, the patient removes brush 31 from its cover (not shown) and breaks open seal 41 with, for example, a fingernail. As shown in FIG. 8, the patient squeezes body 35 so as to force medicament M from the brush body to the brush head 33 via channel 39. A small quantity of the medicament is thus deposited on the brush head and the patient then proceeds to insert the brush head in the interdental spaces and to force the brush head below the gingiva so as to directly apply the medicament to the infected site, as shown in FIG. 9.

Referring to FIG. 10, another delivery device 42 for the medicament is illustrated. Specifically, this delivery device comprises a syringe 43 having a curved nozzle 45 terminating in a relatively small bore, but blunt tip. As illustrated in FIG. 11, the tip of nozzle 45 may be pushed below the gingiva so that a small amount of the medicament may be applied directly to the infected peridontal site. Of course, syringe 43 contains a supply of the medicament. It has been found that patients who do not like to use the floss 23 or the interdental brush 31 have, in some instances, preferred the use of a syringe.

In FIG. 12, an alternative embodiment of a syringe for applying the medicament is indicated in its entirety by reference character 47. As opposed to the plastic nozzle 45 provided on syringe 43, this second syringe 47 has a thin, metal tubular applicator 49. As shown in enlarged scale in FIG. 13, the tip of the tubular applicator 49 has one side thereof removed. In use, the applicator tube 49 of syringe 47 is inserted below the gingiva with the open face 51 of the tip of the applicator tube directed towards the tooth. Then, the patient ejects a small quantity of the medicament from the syringe so that the medicament is preferably brought into direct contact with the infected site.

Figure 15:
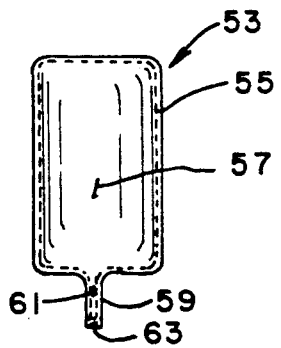
FIG. 15 illustrates a disposable packet holding a supply of medicament and having a tear-open applicator tab.
Figure 16:
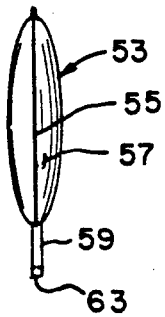
FIG. 16 is a side view of the packet shown in FIG. 15.
Figure 17:
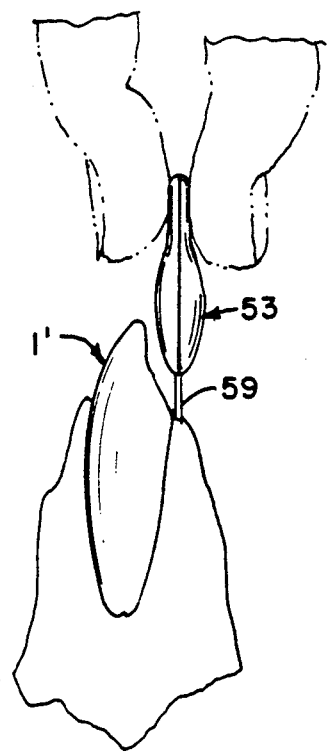
FIG. 17 is a view of a tooth and the packet shown in FIGS. 15 and 16 illustrating the applicator tab inserted beneath the gingiva delivering the medicament to the infected site.

Referring to FIGS. 15-17, still another delivery device is illustrated. This delivery device comprises a flexible packet 53 formed of suitable heat sealable plastic film or the like heat sealed around its margins, as indicated by 55, so as to define a chamber 57 therewithin for holding a supply of the medicament. At one end of packet 53, an applicator nozzle or tab 59 is provided. The plastic film is heat sealed in such a manner as to define a delivery channel 61 within application tab 59 leading from the medicament chamber 55 to the end of the applicator nozzle. A tear-off seal 63 is provided for maintaining the packet in its sealed condition until ready for use. In use, the seal 63 is broken thereby to open channel 61. The patient then inserts the applicator tab 59 below the gingiva and, as illustrated in FIG. 17, squeezes the packet so as to forcibly dispense a small quantity of the medicament into direct contact with the infected site of the teeth. Of course, this is repeated until all of the patient's teeth have been treated and then the packet may be thrown away.

Figure 18:
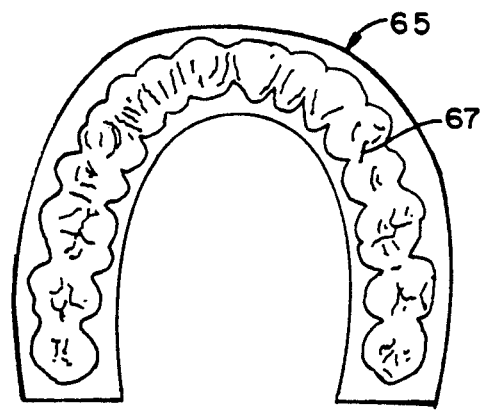
FIG. 18 is a top plan view of an applicator tray having teeth recesses molded from the teeth, a supply of medicament received in the recesses being brought into contact with the teeth for night wear.
Figure 19:
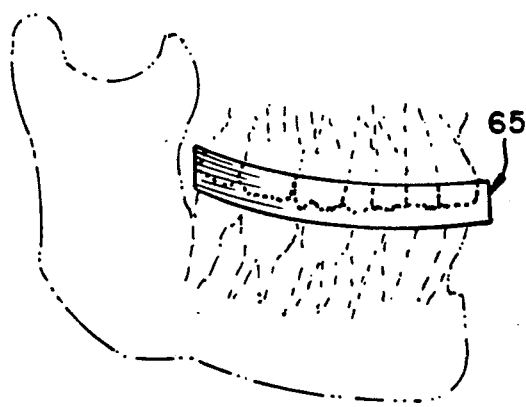
FIG. 19 is a side elevational view of the tray shown in FIG. 18 as it is worn.

Referring to FIGS. 18 and 19, a form fitted flexible tray, as generally indicated at 65, is illustrated for applying the medicament in accordance with this invention. More specifically, tray 65 is of a suitable soft plastic elastomeric or other suitable material which is molded in place to the patient's teeth so as to form a dental arch recess 67 which conforms closely to a patient's teeth and which firmly and closely fits in place on the patient's teeth. Tray 65 is shown to be a full arch tray, but those skilled in the art will recognize that a partial arch tray or a dual arch tray may be used, if desired.

In use, the patient inserts a small amount of medicament (e.g., tetracycline solution) into recess 67 and fits the arch 65 onto the patient's upper or lower arch (as the case may be), as illustrated in FIG. 19. Mastication forces caused by the patient closing his jaw on the tray forcibly squeezes the medicament along the tooth and into the gingiva to the infected site. Alternatively, prior to placing the medicament (tetracycline) in arch recess 67, a small quantity of an antiseptic cleanser preferably containing hydrogen peroxide (1.5% $H_2O_2$) in a gel base is placed in recess 67. Then, on top of the hydrogen peroxide antiseptic cleanser, the medicament (tetracycline) is placed. Tray 65 is then fitted onto the patient's teeth in the manner shown in FIG. 19. The hydraulic action of the teeth fitting closely within recess 67 tends to move the medicament toward the gingiva of the patient's mouth. As the hydrogen peroxide breaks down, it generates oxygen and water which intends to increase the pressure somewhat within recess 67 and thus forces the medicament below the gingiva and into direct contact with the infected site.

It has also been found that through the use of a hydrogen peroxide antiseptic cleanser as described above, the oxygen rich environment caused by the breakdown of the hydrogen peroxide gel oxygenates the gum tissue and provides an antimicrobial environment for the anaerobic peridontal bacteria, thus significantly reducing the population of such bacteria. Further, since hydrogen peroxide is a bleaching agent, some whitening of the patient's teeth has been noted.

It will further be noted that with the tray 65, other medicaments, including fluoride, dichloride medicaments, or a suitable anti-plaque medication (e.g., an anti-plaque medication containing sodium monoflourophosphate or sanquinria) can be used so as to decrease microbial activities or plaque formation.

It has been observed in vitro that the tetracycline appears to bond with the bony structure in the infected areas so as to remain active even between treatments Specifically, the tetracycline inhibits osteoclastic activity without affecting osteoblastic activity. Thus, it promotes bone regeneration. Because the antibiotic is delivered by flossing, brushing, syringe, or by an arch tray, the patient can readily self-administer the medicament several times each day and need not make time consuming visits to his dentist hygeinist or other health care professional for effective delivery of the medication. Preferably, the medicament should be applied every 8-12 hours at the start of the treatment, then later in the treatment twice a day, and finally 3-4 times a week in a maintenance program. This insures that the benefits of the tetracycline medicament are continuous, which is particularly important at the start of the treatment.

In the following examples, a tetracycline solution available from E. R. Squibb & Sons, Inc. of Princeton, N.J. under the trademark Sumycin Syrup was used. The syrup, a tetracycline oral suspension, contains the tetracycline equivalent of 125 mg of tetracycline hydrochloride in a 5 ml quantity. Of course, within the scope of this invention, other medicaments and other tetracycline solutions of varying strength may be used.

EXAMPLE 1

The patient used floss 23 to deliver the above-noted tetracycline solution. After 28 days, the patient also applied the tetracycline using syringe 40. Initially, of twelve teeth which were measured, eight teeth had average pocket depths of 3 mm or more and were endangered by periodontis. Five of these endangered teeth had average pocket depths of 4 mm or more. Over a six month period of use, in seven of the eight teeth which were originally endangered by periodontis, the depths of the pockets were reduced to 3 mm or less. In the eighth tooth, the pocket depth was reduced from about 7 mm to 3 mm. Four of the endangered teeth had sulci 1-2 mm deep and which remained in this range throughout the treatment. After 6 months, this patient did not require periodontal surgery, whereas without this treatment, it was anticipated that at least some teeth would have had to be structurally supported, treated by surgery, or removed.

EXAMPLE 2

Patient used floss 23 to deliver the above-noted tetracycline solution directly to the infected areas. Initially, six of the nine teeth measured were endangered by periodontis. After 76 days of treatment in accordance with this invention, the patient supplemented the delivery of tetracycline with brush 31. After a 3½ month period of treatment with tetracycline, the depth of the pockets of the endangered teeth decreased to an average 3 mm or less. One other tooth which was measured had a pocket depth which remained in the range of 1-2 mm. This patient did require surgery on teeth numbers 3, 4, 31 and 32 of the fifteen teeth originally endangered by periodontal disease. However, eleven of these endangered teeth did not require surgery which otherwise would have.

EXAMPLE 3

Patient used floss 23 to deliver the above-noted tetracycline solution. After 91 days, the patient supplemented delivery by floss with delivery by interdental toothbrush 31. After 8½ months of tetracycline treatment, the one tooth that had an average pocket depth of more than 3 mm remained constant at an average depth of 3.25 mm. Ten teeth remained in the 1-3 mm range. One tooth increased past an average depth of 3 mm. In this patient, no surgery was required. Without the tetracycline, surgery would have been required on teeth numbers 2, 3, 11, 14, 15 and 19. With this treatment, no surgery was required. After 291 days, the patient complained of problems with the use of the floss 21, continued delivery of the medicament with only an interdental brush similar to brush 31.

EXAMPLE 4

Patient used floss 23 to deliver the above-noted tetracycline. After 21 days, delivery by floss was supplemented with delivery by syringe 43. At 769 days, the delivery by syringe 43 was replaced with delivery by brush 31. Initially, nine teeth of twelve measured were endangered by periodontal disease. After 2 years and 1¼ months of tetracycline therapy, the average pocket depth of one tooth decreased to 3 mm to less. Seven other teeth remained in the 3-4 mm range. However, the pockets in two teeth increased to about 4 mm, and the pockets in three teeth remained in the 2-3 mm range. This patient did not require surgery. Without the tetracycline therapy ten teeth would most likely have required surgery.

EXAMPLE 5

Patient used floss 23 to deliver the above-noted tetracycline throughout the course of treatment. At 83 days patient began use of peridex in conjunction with tetracycline. The peridex was delivered by syringe 43. The use of peridex was discontinued at day 217. At day 285, the patient began to wear tray 65 at night to delivery the tetracycline/hydrogen peroxide medicament discussed above. At day 313, the use of the tray was discontinued. At day 335, delivery of tetracycline by floss 23 was supplemented with delivery by syringe, as discussed above. Tetracycline was prescribed to be administered 2-3 times daily.

To date, approximately forty (40) patients have been treated in accordance with this invention for a time sufficient to determine if the patients benefited from the treatment. The above examples are believed to be representative of the results achieved. However, it will be recognized that not all patients benefited equally from this treatment Based on my past experience, the sample of periodontal patients treated in accordance with this invention represents a typical cross section of periodontal patients. Without treatment of the present invention, nearly all of these patients would have required periodontal treatment or surgery and several would have had to have one or more teeth extracted. However, of the forty (40) periodontal patients treated in accordance with the present invention, only three patients required surgery and only one (1) patient underwent extractions.

It will be recognized that since the treatment of this invention is intended to be self-administered, there are certain patients who, for whatever reasons, would not follow through with the treatment for a time sufficient to determine if these certain patients would benefit from the treatment. Accordingly, the results of these patients who did not follow through with the treatment are not included in the above-noted forty (40) patients reported above.

In view of the above, it will be seen that the several objects of the invention are achieved and other advantageous results are obtained.

As various changes could be made in the above methods and constructions without departing from the scope of the invention, it is intended that all matter contained in the above description or shown in the accompanying drawings shall be interpreted as illustrative and not in a limiting sense.

What is claimed is:

1. A method of treatment for periodontal disease wherein said disease causes deterioration of bone structure around or supporting a patient's teeth, said method comprising the steps of:

delivering a medicament to the bony structure of the teeth affected by periodontal disease using a delivery device capable of being used by the patient without help from a dental professional so as to cause the medicament to at least partially bond with said bony structure thereby to substantially continuously slow osteoclastic activity and to allow a net positive osteoblastic activity and resulting in a net regeneration of the bony structure of teeth; and repeating such delivery of said medicament the extended course of treatment until the bony structure has sufficiently regenerated.

2. The method of claim 1, wherein said step of delivering said medicament includes using a delivery device carrying a supply said medicament sufficient to treat all of the periodontal disease sites of the patient's teeth without re-application of the medicament to the delivery device.

3. The method of claim 1, wherein said step of delivering said medicament comprises flossing the periodontal disease sites with a length of dental floss, said floss having means for holding a supply of said medicament sufficient to treat all of the periodontal disease sites without re-application of the medicament to said floss.

4. The method of claim 1, further comprising the step of subgingvially applying said medicament to the exposed areas proximate said infected sites.

5. The method of claim 1, wherein said medicament is an antimicrobial medicament.

6. The method of claim 5, wherein said antimicrobial medicament is a solution of tetracycline.

7. The method of claim 6, wherein said tetracycline solution has the tetracycline equivalent of about 125 mg of tetracycline hydrochloride in a 5 ml quantity.

* * * * *